United States Patent [19]
Kitaevich et al.

[11] Patent Number: 5,598,269
[45] Date of Patent: Jan. 28, 1997

[54] LASER GUIDED ALIGNMENT APPARATUS FOR MEDICAL PROCEDURES

[75] Inventors: Yuli Kitaevich, Loveland; Neil D. Johnson, Cincinnati, both of Ohio; Michael T. Miller, Pittsford, N.Y.; Alan Brown, Longmeadow, Mass.

[73] Assignee: Children's Hospital Medical Center, Cincinnati, Ohio

[21] Appl. No.: 241,969

[22] Filed: May 12, 1994

[51] Int. Cl.$^6$ ................................................. G01B 11/00
[52] U.S. Cl. ....................... 356/399; 128/653.1; 606/130; 378/206
[58] Field of Search ....................... 128/653.1; 606/130; 378/37, 204–206; 356/399; 250/491.1

[56] References Cited

U.S. PATENT DOCUMENTS

| | | | |
|---|---|---|---|
| 4,117,337 | 9/1978 | Staats | 378/205 |
| 4,242,587 | 12/1980 | Lescrenier | 378/205 |
| 4,255,657 | 3/1981 | Lescrenier | 378/206 |
| 4,259,585 | 3/1981 | Novak et al. | 378/37 |
| 4,293,771 | 10/1981 | Lescrenier | 378/206 |
| 4,426,726 | 1/1984 | Chetham | 378/206 |
| 4,543,091 | 9/1985 | Froning et al. . | |
| 4,638,799 | 1/1987 | Moore . | |
| 4,706,665 | 11/1987 | Gouda . | |
| 4,723,544 | 2/1988 | Moore et al. . | |
| 4,733,661 | 3/1988 | Palestrant . | |
| 4,836,671 | 6/1989 | Bautista | 378/206 |
| 4,930,525 | 6/1990 | Palestrant . | |
| 5,031,203 | 7/1991 | Trecha | 378/205 |
| 5,100,411 | 3/1992 | Koutrouvelis . | |
| 5,102,391 | 4/1992 | Palestrant . | |
| 5,316,014 | 5/1994 | Livingston | 378/37 |

OTHER PUBLICATIONS

A. Magnusson et al., "CT–Guided Core Biopsy Using a New Guidance Device", Acta Radiol 1991; 32: pp. 83–85.

P. R. Frederick et al., "A Light–Guidance System To Be Used For CT–Guided Biopsy", Radiology, vol. 154, pp. 535–536.

G. Onik et al., "CT Body Stereotaxis: An Aid For CT–Guided Biopsies", Sep. 9, 1985, AJR:146, Jan. 1986.

Abstract of Oral Presentation at Radiological Society of North America (RSNA) Meeting, Chicago, IL, Nov. 28–Dec. 3, 1993.

We've Got A Whole New Angle on Core Tissue Biopsies Brochure, Bard Radiology, 1992.

Abstract of Presentation at 36th Annual Meeting of The Society for Pediatric Radiology, N. D. Johnson et al., "CT–guided Percutaneous Treatment of Osteoid Osteoma", May 12–15, 1993.

Bennett X–Ray Technologies Brochure.

A. A. Moss, Chapter 22, "Interventional Computed Tomography", pp. 1087–1128, Computed Tomography Of The Body.

*Primary Examiner*—Marvin M. Lateef
*Assistant Examiner*—Brian L. Casler
*Attorney, Agent, or Firm*—Wood, Herron & Evans P.L.L.

[57] ABSTRACT

A portable laser guided alignment apparatus includes a laser line beam source and a laser fan beam source, with the line beam being in the same plane as the fan beam. The apparatus further includes mechanisms for adjusting the angle of the fan beam relative to a vertical reference plane and for adjusting the angle of the line beam within the plane of the fan beam. Additionally, measurement devices are included to measure the angle of the fan beam relative to the vertical reference plane, and to measure the angle of the line beam relative to a vertical reference line within the fan beam plane. The apparatus provides precise alignment for biopsy tools and other instruments used in standard biopsies, discolysis, stereotaxis, and other medical procedures wherein highly accurate positioning and insertion of instruments into a patient are required.

7 Claims, 6 Drawing Sheets

LASER GUIDED ALIGNMENT APPARATUS FOR MEDICAL PROCEDURES

FIELD OF THE INVENTION

The present invention relates to alignment apparatus, and more particularly to laser guided alignment apparatus for use in medical procedures.

BACKGROUND OF THE INVENTION

A wide variety of medical procedures, including standard biopsies, bone biopsies, mammogram-directed biopsies, stereotaxis, lesion drainage, and discolysis, require extremely accurate placement and insertion of medical instruments (such as needles, localization wires or other biopsy tools). Precision placement and insertion of the instrument throughout the procedure is critical to its success and serves to decrease procedure time, which in turn decreases patient discomfort, and potential for complications.

An initial step in many medical procedures such as biopsies is a CT scan (computerized tomography). This procedure provides the physician with a cross-sectional image of a patient through a "cut" or "scan" plane which shows internal organs, tissues, bony structures and abnormalities. Through the use of CT scans, physicians are able to accurately locate abnormal tissues, tumors, lesions, etc., and then can select the optimum insertion point for the appropriate instrument, whether it is a biopsy needle, drainage catheter or other instrumentation, to extract or otherwise treat the abnormality.

Using available CT scanner technology, both the insertion depth and angle required for a biopsy needle can be ascertained with a very high degree of accuracy. The limitation in actual practice, however, is the accuracy of inserting the biopsy needle by the physician, particularly with respect to insertion angle and plane. Utilizing a trial and error technique, some practitioners initially position the needle or catheter by estimating the desired angle and then slowly advance the needle into the patient's body, taking repeated CT scans during the procedure to determine the actual depth and position of the needle and altering its trajectory as required. This trial and error technique has significant disadvantages, including the relatively long time-frame required, the attendant discomfort to the patient, and increased risk due to repeated punctures and/or poor initial positioning of the instrument. Additionally, the multiple CT scans tie up available CT scan time, which is highly sought after, and increases the patient's exposure to radiation.

Certain advancements have been made which offer improvements over the trial and error method for performing CT-based biopsies and other procedures. For example, U.S. Pat. Nos. 4,638,799 and 4,706,665 relate to mechanical guide apparatus for discolysis and stereotactic procedures, respectively. U.S. Pat. No. 4,723,544 discloses another mechanical guide device for discolysis procedures. U.S. Pat. Nos. 4,733,661, 4,930,525 and 5,102,391 relate to guidance devices for CT-guided drainage and biopsy procedures. U.S. Pat. No. 5,100,411 relates to another stereotactic guidance device. Additionally, the article "CT-Guided Core Biopsy Using A New Guidance Device," A. Magnusson and D. Akerfeldt, *Acta Radiol* 1991; 32: pp. 83–85, discusses a mechanical biopsy guidance device. Generally, the devices disclosed in the above-referenced patents and publication are rigidly fixed to the CT scanner. Such devices have several drawbacks, however, including the requirement of precise attachment and alignment relative to the CT scanner. Furthermore, the device may obstruct the field of operation of the physician, and requires the biopsy procedure to be performed at the location of the CT scanner. Other disclosed devices are separate from the CT scanner, but attach to the ceiling, walls or to the floor. Some devices physically hold the needle or biopsy tool and therefore require sterilization before each use. In addition, some of the above devices provide no means for ensuring accurate placement of the biopsy tool in the scan plane (i.e., transverse to the patient) as they relate only to measuring and maintaining the needle insertion angle relative to a longitudinal vertical plane through the patient.

Yet another system which has been developed is described in "A Light-Guidance System To Be Used For CT-Guided Biopsy," P. Frederick et al., *Radiology*, Vol. 154, pp. 535–536. The system disclosed in this article is based on the principle of two intersecting planes represented by thin sheets of light. The intersection of the planes defines a line which can be positioned to define the correct insertion angle of the biopsy device. In use of this system, the biopsy instrument is held so that during its insertion it casts shadows in both beams of light, thus theoretically assuring that the instrument is following the preselected path of the line defined by the intersection of the two planes. This system has several disadvantages, however, including the requirement of two separate light sources which must be kept in alignment for the system to work properly. This beam-alignment must be made with an extremely high degree of accuracy since the light sources are positioned a considerable distance from the patient. This system presents the additional difficulty of requiring the physician to maintain the biopsy tool in line with the two planes of light simultaneously to create a shadow in each.

Thus, there is a need for a highly accurate, portable guidance or alignment apparatus which does not require sterilization or attachment to or modification of a CT scanner. Such an apparatus should be capable of use at a site remote from the CT scanner, thus freeing up the scanner for use on other patients, while insuring highly accurate positioning and insertion of a needle or other biopsy tool into a patient.

SUMMARY OF THE INVENTION

In its broadest aspects, the present invention relates to a portable, highly accurate laser-guided alignment apparatus for use in medical procedures such as biopsies, stereotaxis, etc. The apparatus can be used remote from the CT scanner, i.e., in an operating room, especially when used for neurosurgical or orthopedic procedures, thereby freeing up valuable CT scanner time. The apparatus has no contact with the biopsy tools and thus there is no requirement for sterilization of the device, and it provides for highly accurate positioning and insertion of the biopsy instrument. Furthermore, the apparatus is designed to be used in procedures based on a vertical or a tilted CT scan plane.

In one embodiment, the invention includes a first laser light source for producing a laser line beam and a second laser light source for producing a laser fan beam. The laser line beam is in the same plane as the laser fan beam. The apparatus further includes a frame for supporting the first and second laser light sources, and may also include a mechanism for adjusting the angle of the laser fan beam relative to a vertical reference plane and a mechanism for adjusting the angle of the laser line beam within the laser fan beam plane. Associated with the laser fan beam is a device for measuring the angle thereof relative to the vertical reference plane, and associated with the laser line beam is a device for measuring the angle thereof relative to a vertical reference line within the laser fan beam plane.

One desirable frame arrangement includes a base, an upright post supported by the base, and a cantilever arm extending outwardly and angularly upwardly from the post. The apparatus may further include a housing for the first and second laser light sources which is slidable along the cantilever arm, for more accurate positioning of the laser light sources.

Alternatively, the frame may include a post adapted to be fixed to the housing of a CT scanner such that the laser fan beam plane is parallel to the scan plane of the CT scanner. With this arrangement, as the CT scanner unit is tilted to perform angled scans, the alignment apparatus is likewise tilted so as to precisely match the angle of the scan plane.

In an alternative embodiment, the apparatus may include a single laser light source which produces a laser line beam, and a beam splitter for splitting the laser line beam into two beams, one of which is used to generate the laser fan beam and the other one of which is used as the laser line beam. Optionally, the line beam and the fan beam are coplanar.

It is contemplated that an embodiment of the present invention having a single laser light source, with or without a beam splitter, could be used in conjunction with a mammography machine. In this context, a laser line beam may be reflected or directly projected at or toward the biopsy or localization target. If desired, a laser fan beam can be used in conjunction with the laser line beam for precision alignment with the mechanical portion of the mammography compression device to ensure correct correlation between the target displayed on the mammogram and the laser line beam. Biopsy or localization would then be guided by the laser line beam.

In use, a practitioner aligns the laser fan beam transverse to the patient, and positions the fan beam to coincide with the scan plane marks which have previously been placed on the patient's body, as by techniques well known in the art. Typically available CT scanners calculate the angle of insertion and the insertion depth of the biopsy instrument once the target (biopsy site) and entry point (skin site) are selected by the practitioner. With this information, the practitioner adjusts the angle of the laser line beam to match the predetermined insertion angle, positions the laser fan beam over the scan plane marks on the patient's body, and points the laser line beam at the skin site, which has also been marked on the patient's body. Thereafter, the practitioner places the tip of the biopsy tool on the marked entry point such that the laser line beam is visible as a bright spot in the center of the opposite or trailing end of the instrument. With this arrangement, the physician can insert the tool with an extremely high degree of accuracy by maintaining the laser line beam coincident with the axis of the instrument. If the tool is moved out of proper alignment with the line beam, and thus off the correct course for the procedure, the practitioner need only reposition the tool so that the line beam again strikes the center of the trailing end of the instrument.

To further aid in use of the alignment apparatus of the present invention as described above, the biopsy tool may be provided with a mirror or other reflective material on its trailing end which receives the laser line beam to reflect the laser line beam back to a sensor adjacent the laser source. If the reflected line beam is not sensed by the sensor to be in correct alignment, then the sensor will so indicate by a suitable alarm or other means, and again the practitioner can simply reposition the instrument into correct alignment.

The principles of the present invention, its objectives and advantages will be further understood with reference to the drawings and the following detailed description.

DETAILED DESCRIPTION OF THE INVENTION

While the details of the present invention, as shown in the accompanying drawings, will be described hereinafter in the context of a standard biopsy procedure and a mammogram-guided biopsy procedure, it will be appreciated by persons skilled in the art that the alignment apparatus of the invention is applicable in a wide variety of medical procedures. Such additional procedures include, but are not limited to, stereotaxis, lesion drainage, discolysis, etc.; i.e., the invention is applicable to procedures which require the accurate placement and insertion of medical instruments such as needles, biopsy tools, localization wires, etc.

Figure 1:
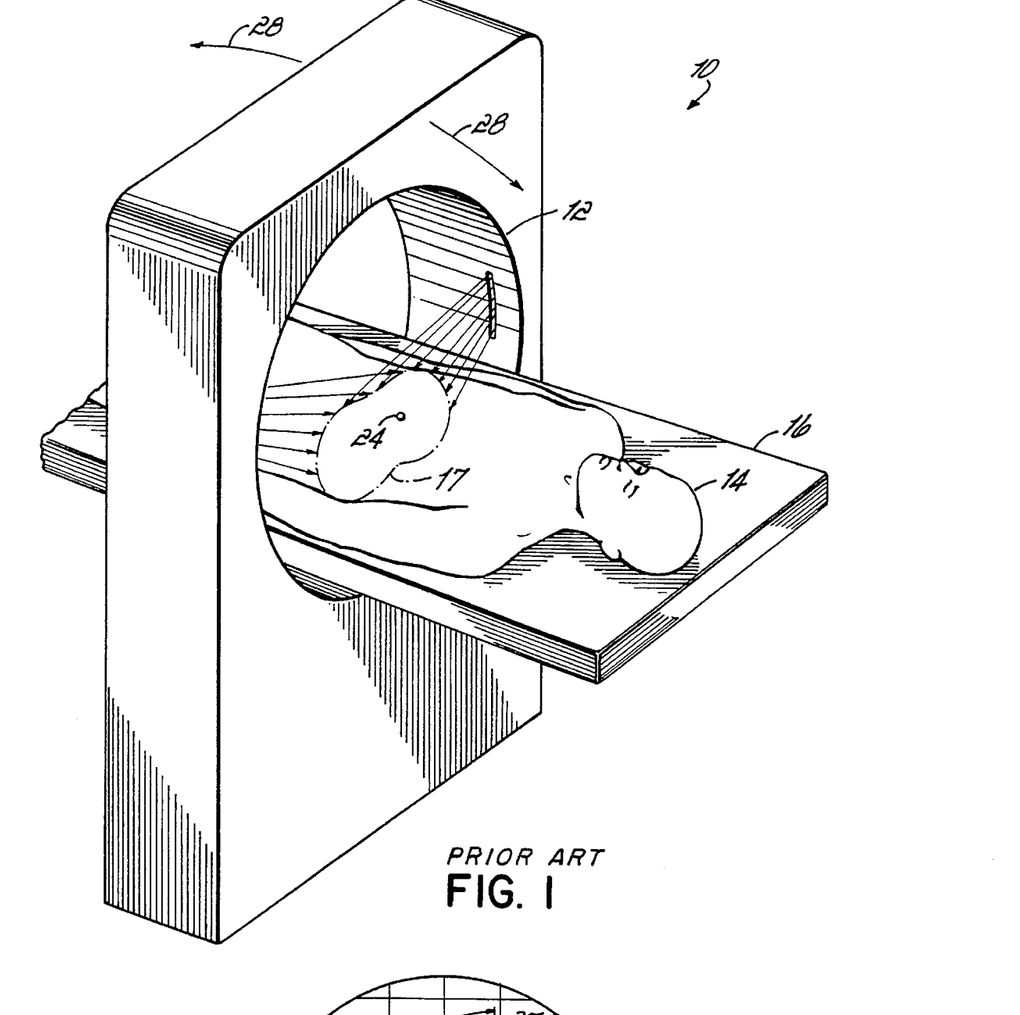
FIG. 1 is a perspective view of a CT scanner scanning a patient.

With reference to FIG. 1, there is shown a CT scanning device 10 having a gantry opening 12 therein which receives a patient 14 supported on a table 16. The mechanical details of CT scanners are well known in the art, as are their operation and method of use, and therefore such details will not be described herein. Suffice it to say that when a patient 14 is scanned within gantry 12, CT scanner 10 generates a cross-sectional image of the patient through a scan plane, represented in FIG. 1 at 17. Typically, CT scanners are provided with a laser or other light source about the internal perimeter of the gantry so as to direct light beams at the patient which are coplanar with scan plane 17. Such beams are visible on the patient's skin and typically the physician will actually mark, using a pen or other marker, the patient's skin at the location of scan plane 17 for reference purposes. As will be appreciated, CT gantry 12 may be tilted such that scan plane 17 through the patient is at an angle with respect to a vertical reference plane. This tilt feature is represented by arrows 28 in FIG. 1.

Figure 1A:
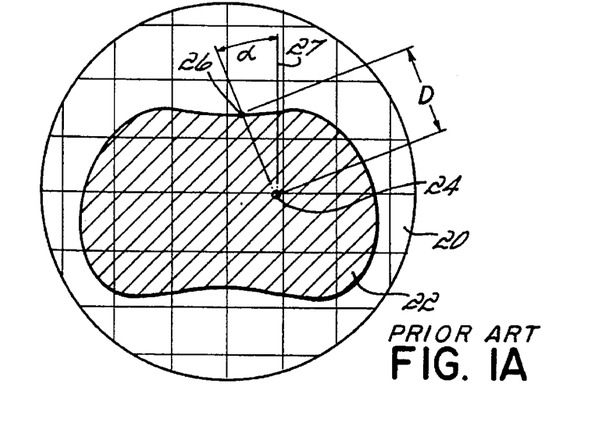
FIG. 1A is a representation of a CT scan image through a patient.

FIG. 1A is a representation of a typical image visible on a CRT display 20 associated with CT scanner 10. Display 20 includes a cross-sectional image 22 of the patient through scan plane 17. By viewing multiple scans through the patient at different locations, the physician is able to pinpoint the tumor, lesion or other patient abnormality designated generally as 24 in FIG. 1A. Also viewing the display, the physician is able to select the appropriate entry point or skin site 26 through which the biopsy instrument (not shown) should be inserted. This site 26 will be selected based on numerous factors, including the location of organs, bones, etc., which may influence the path of the biopsy tool. As is standard in most commercially available CT units, the CT unit will automatically calculate the insertion angle $\alpha$ relative to a vertical reference line 27 and the insertion depth D required to perform the biopsy, based on the location of skin site 26 and target abnormality 24. Furthermore, if gantry 12 is tilted for scanning, the angle of the scan plane relative to vertical is known. Thus, at the conclusion of the CT procedure, the physician is armed with the insertion angle $\alpha$ which is the angle from vertical, the required insertion depth D to which the biopsy instrument must be inserted, as well as any tilt angle relative to a transverse vertical reference plane (not shown) through patient 14. Additionally, the patient's skin will be physically marked at the precise location of scan plane 17 and entry site 26.

Figures 2, 3:
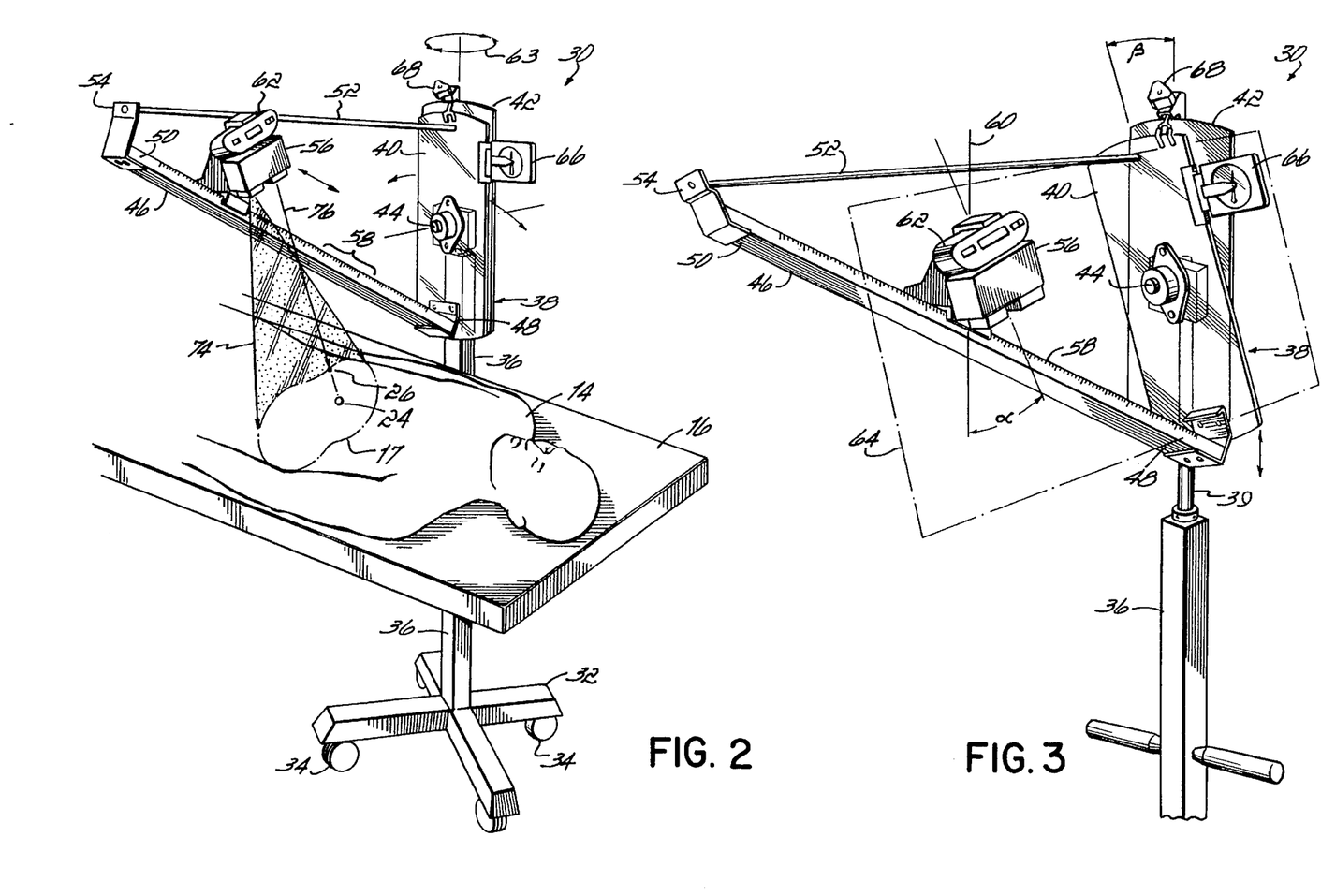
FIG. 2 is a perspective view of one embodiment of the apparatus of the present invention.
FIG. 3 is a perspective view, partially broken away, of the apparatus of FIG. 2 shown in a different orientation.

Utilizing the apparatus of the present invention, which is portable, allows the patient to be moved out of the CT gantry 12 and even from the CT scan room altogether to a remote location. FIG. 2 shows a patient 14 supported on table 16. Alignment apparatus 30 of the present invention is a portable apparatus and is brought into proximity with the patient 14.

As shown in FIG. 2, alignment apparatus 30 has a base 32, which may be on rollers 34 to facilitate the portability of the apparatus. An upright post 36 is supported by base 32 and extends upwardly to support an upper frame structure 38. As shown, upper frame 38 comprises a pair of confronting plates 40, 42 which are pivotable with respect to one another about pivot axle 44. Plate 40 includes a cantilever arm 46 extending outwardly and angularly upwardly therefrom. Cantilever arm 46 is affixed at its proximal end 48 to first plate 40 and is supported at its distal end 50 by a support bar 52 and bracket 54. Alignment apparatus 30 further includes a housing 56 which houses one or more laser light sources, as will be described in detail below. Housing 56 is slidable along cantilever arm 46, which may have calibrated indicia 58 thereon.

Alignment apparatus 30 of the present invention preferably includes various adjustment and measurement features which will now be described with reference to FIG. 3. More particularly, laser light housing 56 is pivotable about an axis (not shown) such that the laser light can be directed at an angle $\alpha$ with respect to a vertical reference line 60. Housing 56 preferably includes an angle measuring device such as an electronic protractor 62 which automatically displays the angle $\alpha$. Furthermore, as stated previously, plate 40 is pivotable with respect to plate 42 about axle 44. This adjustment feature permits the laser light emitted from housing 56 to be adjusted relative to a vertical reference plane 64 since housing 56 is mounted on cantilever arm 46, which is, in turn, rigidly fixed to plate 40. The tilt angle of plate 40 relative to plate 42 is represented by the angle $\beta$ shown in FIG. 3 and may be measured by a suitable measuring device, such as hydraulic protractor 66, affixed to plate 40. In other words, as plate 40 is tilted off of vertical, hydraulic protractor 66 will register the tilt angle $\beta$. A clamp 68 is secured to plate 42 and is used to secure plate 40 so as to maintain the tilt angle $\beta$. Also, the entire upper frame structure 38 can be raised and lowered by telescoping arm 39 in or out of post 36. Additionally, upper frame 38 can be pivoted or rotated about arm 39 as shown in FIG. 2 with reference numeral 63 so as to simplify or aid in positioning of the laser light source 56 with respect to the scan markings and entry site on the patient.

Figure 4:
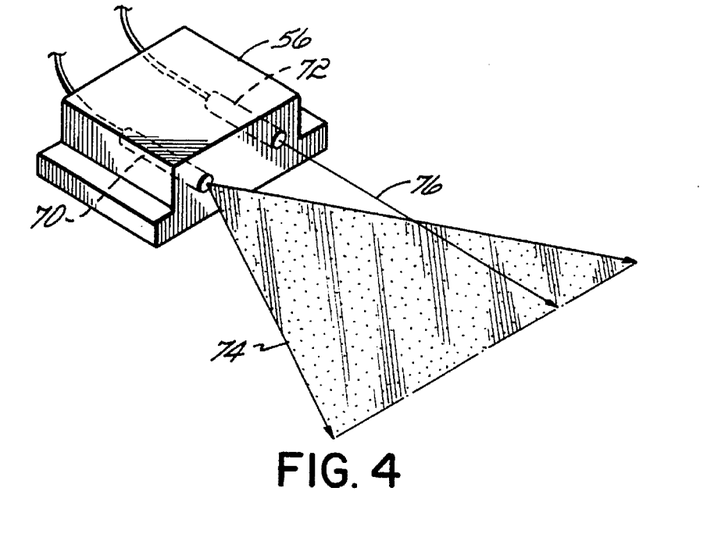
FIG. 4 is a perspective view of one embodiment of a laser light source used in the present invention.
Figure 5:
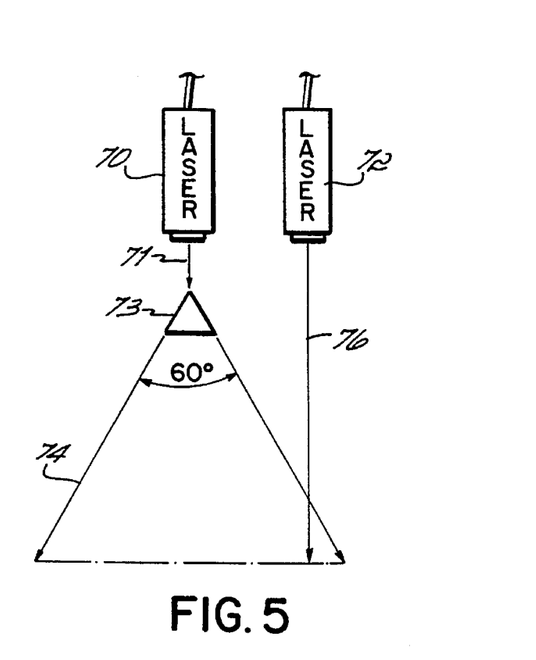
FIG. 5 is a schematic representation of the laser light source shown in FIG. 4.

FIG. 4 shows one embodiment of laser light housing 56 wherein two laser light sources 70 and 72 are maintained in close proximity to one another. Suitable laser light sources are laser diodes, such as are available from Applied Laser Systems, Grants Pass, Oreg. As shown schematically in FIG. 5, laser light source 70 emits a line beam 71 which passes through a prism 73 to produce a fan beam 74, which may preferably have a fan angle of 60°. Second laser light source 72 produces a line beam 76 which lies in the same plane as fan beam 74. That plane will be referred to as the laser fan beam plane (not explicitly shown).

Figure 6:
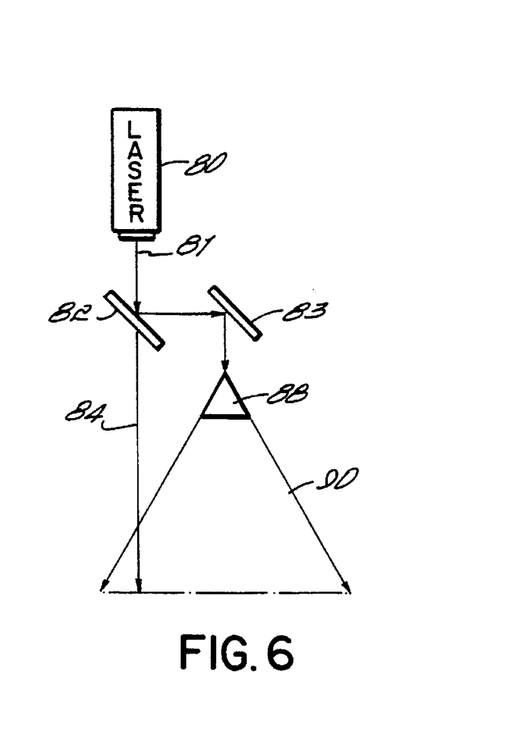
FIG. 6 is a schematic representation of an alternative embodiment of a laser light source used in the present invention.

FIG. 6 shows a schematic of an alternative laser light source wherein a single laser light source 80 is utilized which produces a line beam 81 that is split by beam splitter 82, resulting in a first line beam 84 and a second line beam 86. The second line beam 86 is reflected by mirror 83 to pass through prism 88, resulting in fan beam 90.

Having thus described the structural details of alignment apparatus 30, its method of use will now be described with reference to FIGS. 2 and 3. Alignment apparatus 30 is brought into proximity with a patient 14 having scan plane markings (not shown) on the skin which represent CT scan plane 17. If the CT scan was taken in a vertical plane, then no adjustment of alignment apparatus 30 is required relative to vertical reference plane 64 and the apparatus is maintained in the upright, vertical orientation shown in FIG. 2. However, if a tilted CT scan was taken, alignment apparatus 30 must be adjusted by pivoting plate 40 relative to plate 42 to correspond to the predetermined angle $\beta$ of the tilted scan. This will ensure that laser fan beam 74 and laser line beam 76 are coincident with scan plane 17. Thereafter, housing 56 is tilted such that the angle $\alpha$, as shown in FIG. 3 and measured by measuring device 62, matches the angle $\alpha$ calculated by CT scanner 10 and shown in FIG. 1A. Then, housing 56 is slid (up or down) along cantilever arm 46 to the appropriate location such that the visible spot created by laser line beam 76 is pinpointed on the entry site 26 marked on the patient's skin. With this arrangement, the precise angle necessary for the biopsy tool to reach its target 24 is defined by the line beam 76.

The physician then places the tip of a biopsy tool (not shown) on skin site 26 and positions the trailing end of the tool so that laser line beam 76 is visible as a bright spot in the center of the tool end. The operator maintains the laser spot on the trailing end of the tool as the tool is inserted precisely along a line coincident with laser line beam 76. Providing the operator maintains the laser spot on the trailing end of the tool, the correct insertion angle is achieved and the device is then inserted to the proper insertion depth, to accurately pinpoint the patient abnormality 24.

Figures 7, 8:
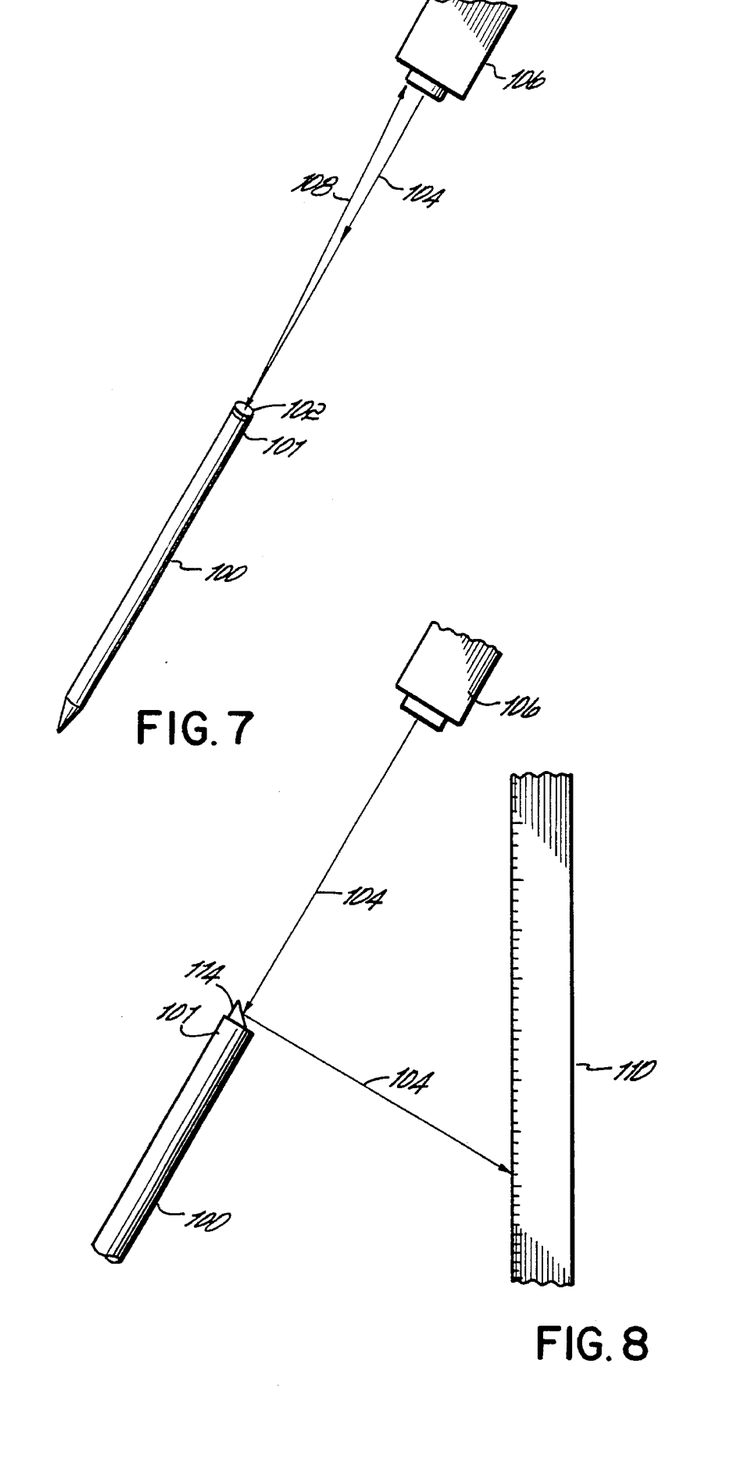
FIG. 7 is a perspective view of a biopsy tool being used in conjunction with the apparatus of the present invention to ensure proper alignment of the tool during use.
FIG. 8 is an alternative configuration of a biopsy tool being used in connection with the present invention to measure the insertion depth of the instrument.

With reference to FIG. 7 there is shown a biopsy instrument 100 which has affixed to its trailing end a reflective material or mirror 102 for reflecting laser line beam 104 from laser light source 106. As explained above, the operator maintains the instrument positioned such that the laser line beam strikes the trailing end of the instrument to ensure proper alignment thereof. To aid in maintaining such alignment, laser light source 106 may be provided with a sensor (not specifically shown) for sensing the reflected beam 108. When the biopsy tool is misaligned, the reflected or return beam 108 will not be sensed by the sensor and an alarm will be generated signaling the misalignment to the operator. Upon correction of the misalignment, the sensor will once again sense return beam 108 and the operator will be assured of proper positioning of the instrument.

FIG. 8 shows an arrangement whereby the insertion depth of biopsy tool 100 may be monitored on a calibrated scale 110, which may be mounted on upright post 36 or freestanding. In this arrangement, the trailing end 101 of instrument 100 is provided with a prism or angled mirror 114 that reflects laser line beam 104 in a perpendicular direction to strike graduated scale 110, as shown. As instrument 100 is inserted into the patient, the reflected beam 104 will move down along ruler 110 a distance proportional to the insertion depth, thereby indicating the depth of insertion of instrument 100.

Figure 9:
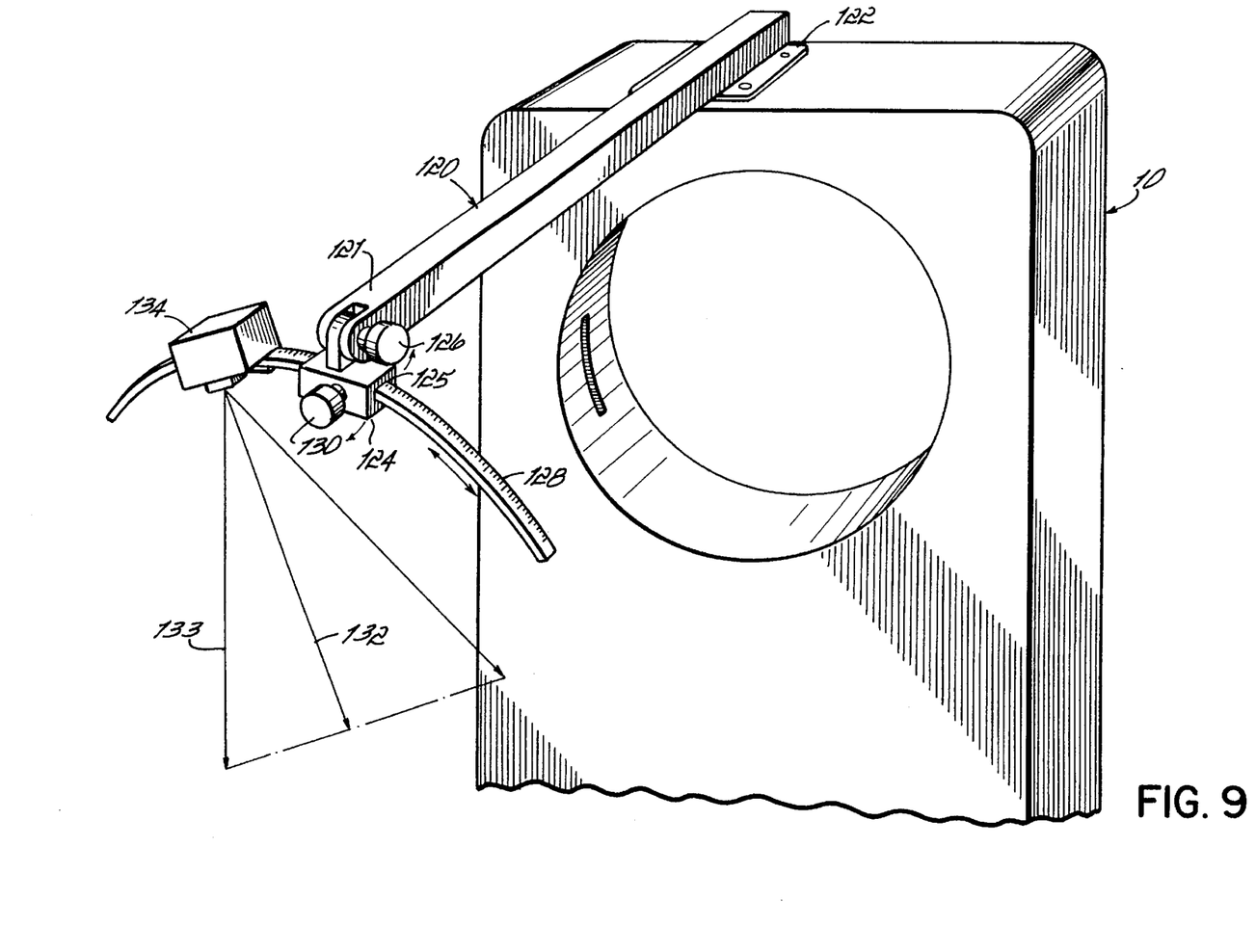
FIG. 9 is a perspective view of a CT scanner with an alternative apparatus of the present invention affixed thereto.

FIG. 9 shows an alternative embodiment of an alignment apparatus of the present invention wherein a support post 120 is rigidly affixed to a CT scanner 10 as by bracket 122. At the terminal end 121 of post 120 there is a guide member 124, pivotable about axle 126. Additionally, the alignment apparatus includes an arcuate, calibrated member 128 which is slidably receivable through a slot 125 in guide member 124. By means such as set screw 130, member 128 can be positioned in an appropriate position such that line beam 132 emitted from laser light source 134 is at the desired angle relative to vertical, as required for the biopsy or other procedure. Laser light source 134 may be the same as that shown in FIGS. 2–6; i.e., it produces both a laser line beam 132 and a laser fan beam 133, which are coplanar. In this embodiment, due to the rigid affixation of the device to CT scanner 10, as the scanner is tiled to perform a non-vertical scan through the patient, the alignment device will likewise be tilted at the same angle relative to a vertical reference plane transverse to the patient. In use, the operator follows the same procedure of aligning the biopsy tool with line beam 132 as described hereinabove.

Figure 10:
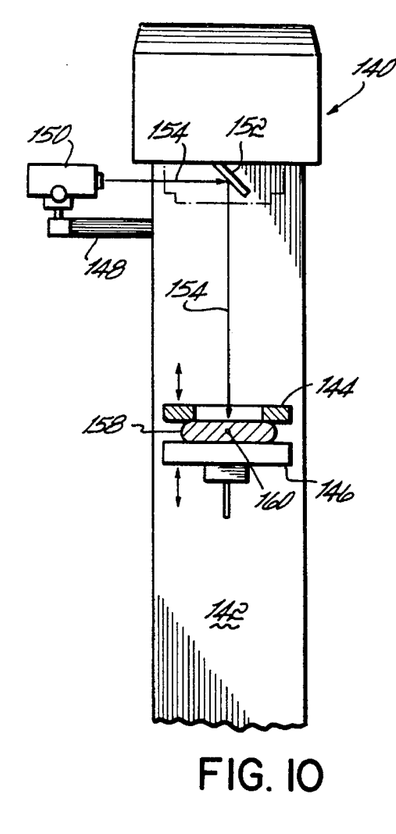
FIG. 10 is a schematic front elevation, partially broken away, of a mammography machine having a laser alignment apparatus affixed thereto.
Figure 11:
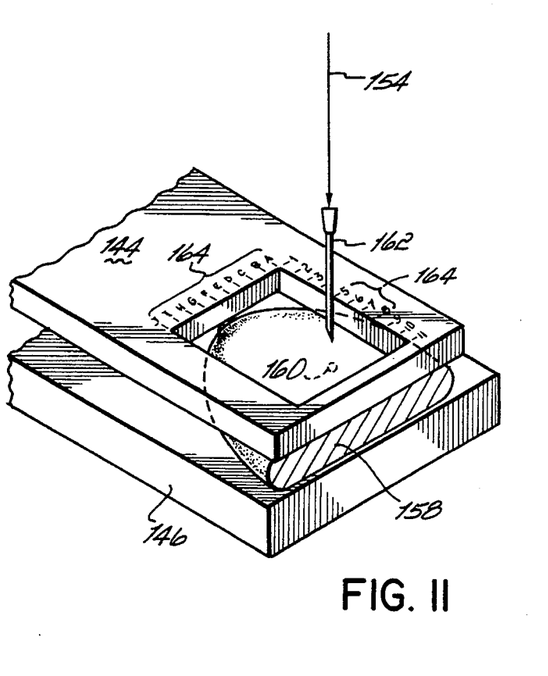
FIG. 11 is a perspective view, partially broken away, of a portion of a mammography machine, showing laser guidance of a biopsy or localization needle.

Finally, another alternative embodiment of an alignment device of the present invention is shown in FIGS. 10 and 11. Mammography machine 140, the details of which are known in the art and will not be described in detail, has an upstanding post 142 on which clamping paddles 144 and 146 are vertically movable, as shown by the arrows. Post 142 further includes a support arm or bracket 148 to which is affixed laser light source 150. Mammography machine 140 will generally have a mirror 152 associated therewith. If it does not, a suitable mirror can be retrofitted to the machine as an add-on in conjunction with the alignment apparatus. Laser light source 150 emits a laser line beam 154 directed at mirror 152 which in turn reflects beam 154 vertically downwardly toward the breast section compressed between paddles 144 and 146. Laser light source 150 is affixed to support arm 148 to permit pivoting in both a horizontal and vertical direction so that the line beam 154 can be directed at the biopsy target 160 which has previously been located within breast segment 158. The operator then utilizes a biopsy needle 162 to either perform the biopsy or insert a localization wire to "tag" the biopsy target for later removal in another procedure. The biopsy tool 162 is maintained in proper alignment to reach its target 160 by maintaining line beam 154 as a bright spot in the center of the trailing end 163 of biopsy tool 162. It will be appreciated, that the specific configuration shown in FIG. 10 is exemplary only and various other locations and means for attaching a laser source to a mammography machine are contemplated. Additionally, if necessary, laser light source 150 may also include a laser fan beam to further aid in the alignment of the biopsy needle with respect to the calibrated grid 164 on upper compression paddle 144.

While the present invention has been described with reference to preferred embodiments, it will be understood by those skilled in the art that various changes may be made and equivalents may be substituted for elements thereof without departing from the scope of the invention. In addition, modifications can be made to adapt the apparatus for use in various medical procedures other than the biopsy procedures described in detail herein, in accordance with the teachings of the invention and without departing from the essential scope thereof.

What is claimed is:

1. A laser guided alignment apparatus for medical procedures, comprising:

a first laser light source for producing a laser line beam;

a second laser light source for producing a laser fan beam, said laser line beam being in a same plane as said laser fan beam; and a frame for supporting said first and second laser light sources;

means for adjusting an angle of said laser fan beam relative to a vertical reference plane; and means for measuring the angle of said laser fan beam relative to said vertical reference plane.

2. Alignment apparatus according to claim 1 further comprising:

means for adjusting a angle of said laser line beam within said laser fan beam plane.

3. Alignment apparatus according to claim 2 further comprising:

means for measuring the angle of said laser line beam relative to a vertical reference line within said laser fan beam plane.

4. Alignment apparatus according to claim 1, said frame including:

a base;

an upright post supported by said base; and a cantilever arm extending outwardly and angularly upwardly from said post.

5. Alignment apparatus according to claim 4 further comprising:

a housing in which said first and second laser light sources are disposed, said housing being slidable along said cantilever arm.

6. A laser guided alignment apparatus for medical procedures, comprising:

a first laser light source for producing a laser line beam;

a second laser light source for producing a laser fan beam, said laser line beam being in a same plane as said laser fan beam;

a frame for supporting said first and second laser light sources, said frame including:

a base, an upright post supported by said base, and a cantilever arm extending outwardly and angularly upwardly from said post;

means for adjusting an angle of said laser fan beam relative to a vertical reference plane;

means for measuring the angle of said laser fan beam relative to said vertical reference plane;

means for adjusting an angle of said laser line beam within said laser fan beam plane; and means for measuring the angle of said laser line beam relative to a vertical reference line within said laser fan beam plane.

7. Alignment apparatus according to claim 6 further comprising:

a housing in which said first and second laser light sources are disposed, said housing being slidable along said cantilever arm.

* * * * *